(12) United States Patent
Cheng

(10) Patent No.: US 11,096,841 B2
(45) Date of Patent: Aug. 24, 2021

(54) WOODPULP-FREE URINE PAD AND THE PRODUCTION EQUIPMENT

(71) Applicant: Wuhu leisurely nursing supplies Polytron Technologies Inc, Wuhu (CN)

(72) Inventor: Gang Cheng, Wuhu (CN)

(73) Assignee: WUHU LEISURELY NURSING SUPPLIES POLYTRON TECHNOLOGIES INC, Wuhu (CN)

( * ) Notice: Subject to any disclaimer, the term of this patent is extended or adjusted under 35 U.S.C. 154(b) by 516 days.

(21) Appl. No.: 15/870,028

(22) Filed: Jan. 12, 2018

(65) Prior Publication Data
US 2019/0183692 A1 Jun. 20, 2019

(30) Foreign Application Priority Data
Dec. 20, 2017 (CN) .......................... 201711387714.2

(51) Int. Cl.
| | |
|---|---|
| A61F 13/00 | (2006.01) |
| A01L 1/00 | (2006.01) |
| A61F 13/53 | (2006.01) |
| A61F 13/47 | (2006.01) |
| A61F 13/15 | (2006.01) |

(Continued)

(52) U.S. Cl.
CPC ............ *A61F 13/53* (2013.01); *A01K 1/0107* (2013.01); *A01K 1/0157* (2013.01); *A61F 13/15658* (2013.01); *A61F 13/47* (2013.01); *A61F 2013/15146* (2013.01); *A61F 2013/530481* (2013.01); *A61F 2013/53908* (2013.01); *Y10T 156/1056* (2015.01)

(58) Field of Classification Search
None
See application file for complete search history.

(56) References Cited

U.S. PATENT DOCUMENTS

| | | | | |
|---|---|---|---|---|
| 3,587,931 A | * | 6/1971 | Studer | .................... A01D 46/00 222/622 |
| 2006/0016392 A1 | * | 1/2006 | Nojo | .................... B05C 1/0817 118/258 |

(Continued)

*Primary Examiner* — Linda L Gray
(74) *Attorney, Agent, or Firm* — Chun-Ming Shih; Lanway IPR Services

(57) ABSTRACT

A woodpulp-free urine pad includes from top to bottom a top sheet, a perforated film layer, a core layer and a bottom layer, wherein the perforated film layer is made by perforating the surface of the waterproof material, the core layer comprises an upper adhesive layer, a lower adhesive layer and a water accepting layer which is mad of SAP polymeric particle between the upper and lower adhesive layers. The utility model has a strong ability to prevent liquid infiltration, and it removes away the wood pulp in the core layer to save a large amount of wood and to protect the environment. A production equipment for producing the woodpulp-free urine pad includes a feeding channel which is composed of a plurality of back-up rolls, follow the direction of forward motion of the feeding channel, there is sequentially provided with a material shelf of lower adhesive layers, an adding mechanism of water accepting layers, a material shelf of upper adhesive layers, a material shelf of bottom layers, a material shelf of top sheet and a cutting table, in order to facilitate the production of the woodpulp-free urine pad.

2 Claims, 3 Drawing Sheets

(51) Int. Cl.
*A01K 1/015* (2006.01)
*A01K 1/01* (2006.01)
*A61F 13/539* (2006.01)

(56) References Cited

U.S. PATENT DOCUMENTS

2006/0278335 A1* 12/2006 Moriura ............ A61F 13/15658
156/279
2009/0233046 A1* 9/2009 Iulianetti .................. B26F 1/24
428/137

* cited by examiner

WOODPULP-FREE URINE PAD AND THE PRODUCTION EQUIPMENT

BACKGROUND OF THE INVENTION

1. Technical Field

This utility model relates to the technical field of urine pad products and the technical field of the production equipment of urine pad, to be specific, a woodpulp-free urine pad and its production equipment.

2. Description of Related Art

Urine pad, a kind of pad with liquid adsorption function, is widely used as house pet mat, nursing napkin and so on.

The core structural material of ordinary urine pads is a mixture of wood pulp and highly absorbent polymer wrapped by bathroom tissues. Due to the water-absorbing quality of these two materials, liquid infiltration easily appears after adsorbing urine.

Products with the core structural material mixed by wood pulp and macromolecules and wrapped by double-layer bathroom tissues cannot resist liquid infiltration after adsorbing liquid, since bathroom tissues adsorb liquid with the hollow structure of the fiber. The thickness of bathroom tissues is only 0.05 mm, a large amount of wood pulp is needed to fill the core in order to provide a space for SAP to form a certain thickness of the urine pads, which causes great consumption of wood resources.

SUMMARY OF THE INVENTION

Because of the deficiencies of the above-mentioned existing technology, the utility model discloses a woodpulp-free urine pad and its production equipment, and is aimed at solving the technical problems in the above-mentioned technical field.

The technical problems are solved by the utility model with the following technical schemes.

A woodpulp-free urine pad, comprising from top to bottom a top sheet, a perforated film layer, a core layer and a bottom layer, wherein the perforated film layer is made by perforating the surface of the waterproof material, the core layer comprises an upper adhesive layer, a lower adhesive layer and a water accepting layer which is mad of SAP polymeric particle between the upper and lower adhesive layers.

As a further improvement of the utility model, the perforated film layer is made of PE material, PP material or the mixed material of PE and PP.

As a further improvement of the utility model, the thickness of the perforated film layer is 0.1-0.3 mm and the perforation rate is 30-40%.

As a further improvement of the utility model, the perforated film layer is perforated in a funnel type with the large diameter end facing to the top sheet.

As a further improvement of the utility model, the top sheet is made of non-woven fabrics, the upper and lower adhesive layers are made of bathroom tissues and the bottom layer is made of PE film.

A production equipment for producing the woodpulp-free urine pad in regard to claim 1 is characterized in that it comprises a feeding channel which is composed of a plurality of back-up rolls, follow the direction of forward motion of the feeding channel, there is sequentially provided with a material shelf of lower adhesive layers, an adding mechanism of water accepting layers, a material shelf of upper adhesive layers, a material shelf of bottom layers, a material shelf of top sheet and a cutting table, including a material shelf of perforated film layers which is located between the material shelf of upper adhesive layers and the material shelf of top sheet.

As a further improvement of the utility model, the adding mechanism of water accepting layers comprises a material addition roller, which is equipped with a collecting hopper on the top and several pits on the outer surface for holding a single polymeric particle. The lowest end of the material addition roller is tangent to the feeding channel.

As a further improvement of the utility model, it also comprises a perforation roller which is located between the material shelf of perforated film layers and the back-up roller under it.

As a further improvement of the utility model, the perforation roller is an electric heating roller which is covered with a thermal-protective coating on the outer surface. A plurality of conical protrusions on the perforation roller cut through the thermal-protective coating.

The utility model has the following beneficial effects.

The woodpulp-free urine pad provided by the utility model is designed a perforation layer between the core layer and the top sheet which is made of waterproof material with a strong ability to resist the liquid infiltration. Besides, the wood pulp in the core layer is removed to save a large amount of wood and to protect the environment. The utility model has also designed a production equipment for producing the woodpulp-free urine pad to conveniently realize the production of the above-mentioned woodpulp-free urine pad.

DETAILED DESCRIPTION OF THE INVENTION

The specific mode of execution of the utility model, such as the shape, structure, the position and connection of each part, the function and working principle of each part, the manufacturing process and operation methods, etc., is further explained in detail with the following description of examples, to help the technical personnel in the field to have a more complete, accurate and in-depth understanding of the inventive conception and technical scheme of the utility model.

Figure 1:
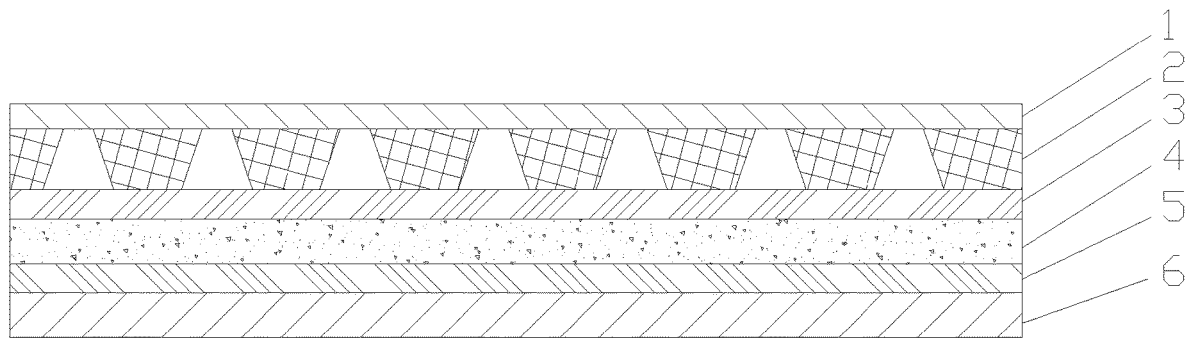
FIG. 1 is a principal view of the woodpulp-free urine pad of the utility model.

As shown in FIG. 1, a woodpulp-free urine pad, comprising from top to bottom a top sheet 1, a perforated film layer 2, a core layer and a bottom layer 6.

The top sheet 1 is directly in contact with human or animal skins, which adopts skin friendly materials, for example, the non-woven fabrics, to meet the requirements of comfort.

The perforated film layer 2 is made of water proof materials with perforation on the surface, for example, PE, PP materials or mixture of PE and PP materials. The optimized thickness of the perforated film layer 2 is 0.1-0.3 mm and the perforation rate is 30-45%. It is preferred to be perforated in a funnel type with the large diameter end facing to the top sheet. When the pad is squeezed, the water that is extruded from the core layer can be temporarily stored in the hole of the perforated film layer 2. The funnel-shaped aperture can store more water, which improves the ability to prevent liquid infiltration.

The core layer comprises the upper adhesive layer 3, the lower adhesive layer 5 and the water accepting layer 4 which is made of superabsorbent polymer (SAP). The upper adhesive layer 3 and the lower adhesive layer 5, which are made of permeable material, for example, the bathroom tissue, wrap the polymeric particles evenly.

The bottom layer 6 is made of water proof material, for example, the PE film.

Wood pulp is needed to increase the thickness of traditional urine pads. On account of the thickness of 0.1-0.3 mm of the perforated film layer 2, the woodpulp-free urine pad is thick enough to meet the requirements of comfort.

Figure 2:
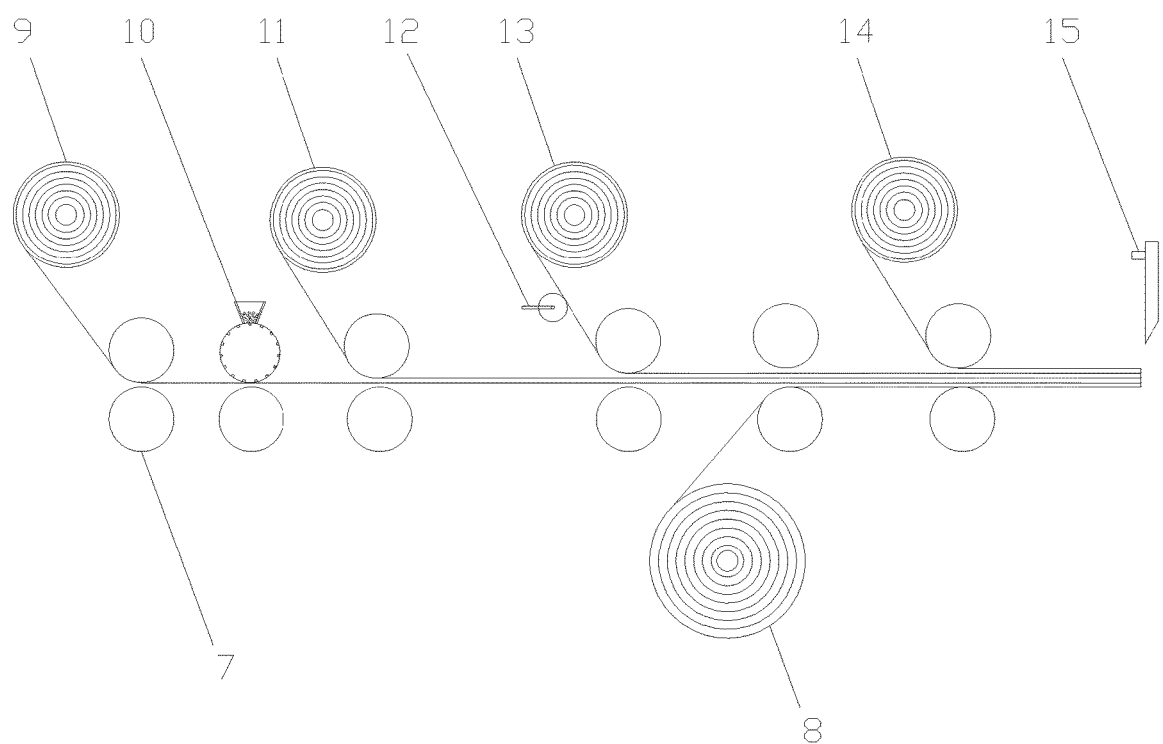
FIG. 2 is a production equipment (including the perforation roller) of the woodpulp-free urine pad of the utility model.
Figure 3:
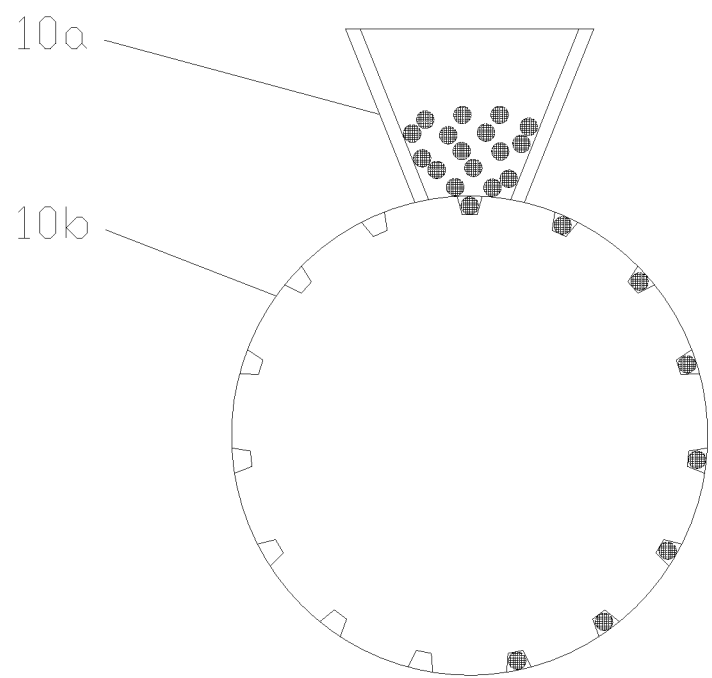
FIG. 3 is a partial schematic diagram of the adding mechanism for water accepting layer in the production equipment of the woodpulp-free urine pad of the utility model.
Figure 4:
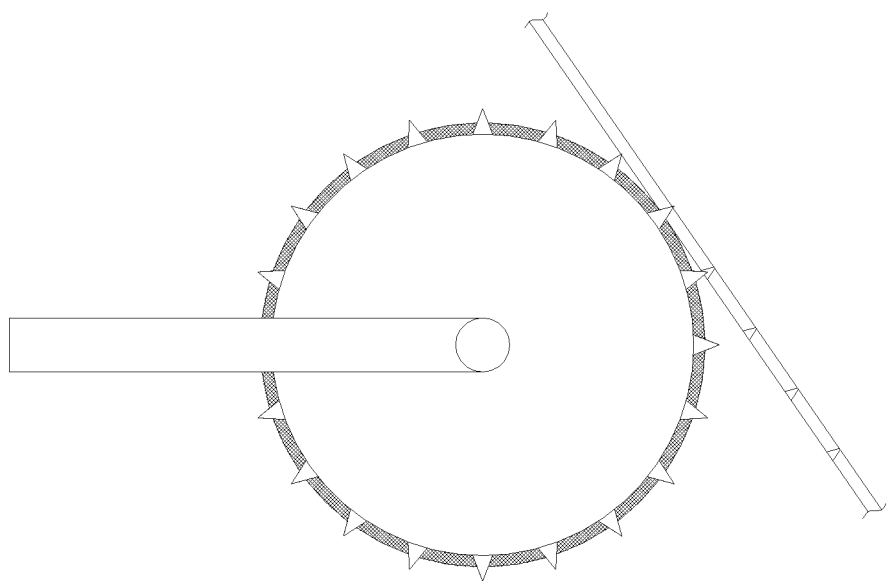
FIG. 4 is a part sketch of the perforation roller in the production equipment of the woodpulp-free urine pad of the utility model production equipment (without the perforation roller) of the woodpulp-free urine pad of the utility model.

As shown in FIG. 2 to FIG. 4, a production equipment for producing the woodpulp-free urine pad comprises the feeding channel which is composed of a plurality of back-up rollers 7, follow the direction of forward motion of the feeding channel, there is sequentially provided with the material shelf 9 of lower adhesive layers, the adding mechanism 10 of water accepting layers, the material shelf 11 of upper adhesive layers, the perforation roller 12, the material shelf 13 of the perforated film layer, the material shelf 8 of bottom layers, the material shelf 14 of top sheet and the cutting table 15. The material shelves 8, 9, 11, 13, and 14 are rollers which are able to hold materials used for producing the woodpulp-free urine pad.

The material shelf 8 of bottom layers is used for placing the PE film rolls; the material shelf 9 of lower adhesive layers and the material shelf 11 of upper adhesive layers are used for placing bathroom tissue rolls; the material shelf 14 of top sheet is used for placing non-woven fabrics.

The adding mechanism 10 of water accepting layers comprises the material addition roller 10b and the collection hopper 10a which is used for placing polymeric particles. Several pits on the outer surface of the material addition roller 10b are used for holding a single polymeric particle. The lowest end of the material addition roller 10b is tangent to the feeding channel. The material addition roller 10b rotates synchronously with the back-up roller 7. When the pits on the material addition roller 10b roll under the collection hopper 10a during the rotation, the polymeric particles in the collection hopper 10a enter into the pits. The material addition roller 10b continues to rotate, when the pits move to contact with the lower adhesive layer 5, the polymeric particles in the pits adhere to the lower adhesive layer 5.

The material shelf 13 of the perforated film layers, which is located between the material shelf 11 of upper adhesive layers and the material shelf 14 of top sheet, is used for placing PE film rolls to be perforated. The perforation roller 12, which is located between the material shelf 13 of the perforated film layers and the back-up roller 7, is in contact with the lower surface of PE film rolls and is used for regular funnel-shaped holes on PE film rolls. The perforation roller 12 is an electric heating roller which is covered with a thermal-protective coating on the outer surface. A plurality of conical protrusions on the perforation roller 12 cut through the thermal-protective coating. The optimized working temperature of the electric heating roller is set to 115-135° C.

The working principle of the production equipment of the woodpulp-free urine pad is: the bathroom tissues on the material shelf 9 of lower adhesive layers enter the feeding channel as the lower adhesive layer 5 and move to the bottom of the adding mechanism 10 of water accepting layers. The material addition roller 10b rolls to append regularly the polymeric particles on the bathroom tissues, then the bathroom tissues cover the polymeric particles as the upper adhesive layer 3. The material shelf 13 of perforated film layers is launched to place the perforated film with funnel-shaped holes on the core layer. The PE film on the material shelf 8 of bottom layers enter the feeding channel as the bottom layer 6 and underlay the core layer. The non-woven fabrics overlays on the perforated film layer 2 as the top sheet 1, then is cut off. The woodpulp-free urine pad provided by the utility model is designed a perforated film layer 2 between the core layer and the top sheet, wherein the latter is made of waterproof material with a strong ability of anti liquid infiltration. Besides, the wood pulp in the core layer is removed to save a large amount of wood and to protect the environment. The utility model has also designed a production equipment for producing the woodpulp-free urine pad to conveniently realize the production of the above-mentioned woodpulp-free urine pad.

Figure 5:
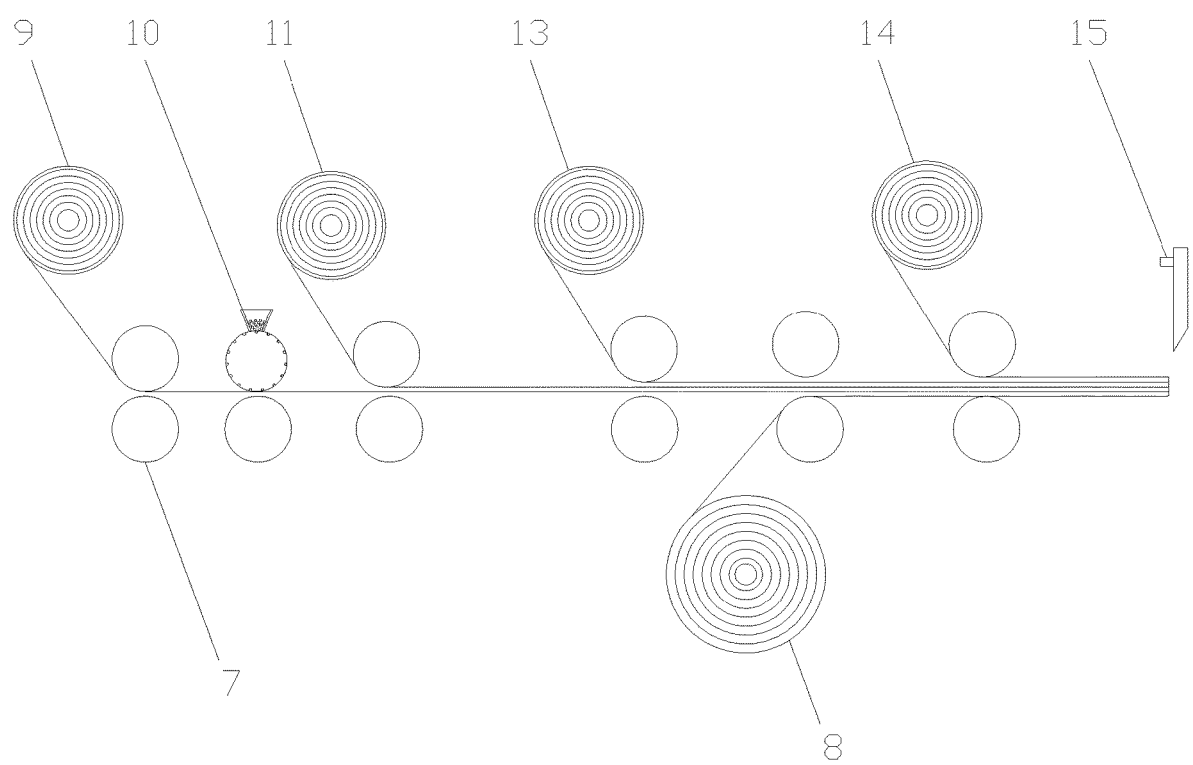
FIG. 5 is another production equipment of the woodpulp-free urine pad of the utility model.

There is another embodiment of the production equipment of the woodpulp-free urine pad, as shown in the FIG. 5, wherein the perforation roller 12 is moved away while the rest is almost the same with FIG. 4. in case of using the second production equipment of the woodpulp-free urine pad, pre-perforated film rolls should be placed on the material shelf 13 of perforation film layers.

The preceding part of the text illustrates that the concrete realization of the utility model is not limited by the above-mentioned method, any non-substantive improvement which adopt the method concept and technical solution of the utility model, or any direct application of the method concept and technical solution of the utility model without improvement for other occasions, are within the protection scope of the present utility model. The protection scope of the utility model should be subject to the protection scope defined by the Claims.

What is claimed is:

1. A production equipment for producing a woodpulp-free urine pad, which is consisted of a feeding channel composed of a plurality of back-up rollers, and following a direction of forward motion in the feeding channel, there being sequentially provided with a material shelf of lower adhesive layer, an adding mechanism of water accepting layer, a material shelf of upper adhesive layer, a material shelf of bottom layer, a material shelf of top sheet and a cutting table, including a material shelf of perforated film layer which is located between the material shelf of upper adhesive layer and the material shelf of top sheet, wherein the material shelf of bottom layer is used for placing polyethylene film rolls, the material shelf of lower adhesive layer and the material shelf of upper adhesive layer are used for placing tissue rolls, and the material shelf of top sheet is used for placing non-woven fabrics;

wherein the adding mechanism of water accepting layer is located between the material shelf of lower adhesive layer and the material shelf of upper adhesive layer, and is consisted of a material addition roller which is equipped with a trapezoid-shaped collecting hopper, containing polymeric particles, on a top of the material addition roller and trapezoid-shaped pits on an outer surface of the material addition roller, when each of the pits for holding a single polymeric particle;

wherein when the pits on the material addition roller roll under the collecting hopper during rotation of the material addition roller, the polymeric particles in the collecting hopper enter into the pits, and the material addition roller continues to rotate, when the pits move to contact with the lower adhesive layer, the polymeric particles in the pits adhere to the lower adhesive layer;

wherein a single perforation roller, which is located between the material shelf of perforated film layer and one back-up roller under the perforation roller, is in contact with a lower surface of the perforated film layer and is used for forming regular funnel-shaped holes on the perforated film layer; and wherein the perforation roller is an electric heating roller which is covered with a thermal-protective coating on an outer surface, and a plurality of conical protrusions on the perforation roller cut through the thermal-protective coating.

2. The production equipment for producing the wood-pulp-free urine pad as claimed in claim 1, wherein a lowest end of the material addition roller is tangent to the feeding channel.

* * * * *